United States Patent [19]

Kita

[11] Patent Number: 5,417,929

[45] Date of Patent: May 23, 1995

[54] ELEMENTS COMBINING DEVICE FOR ENCLOSED STRUCTURES

[76] Inventor: Stanley F. Kita, 27 Wright Ave., Lindenwold, N.J. 08021

[21] Appl. No.: 158,413

[22] Filed: Nov. 29, 1993

[51] Int. Cl.⁶ .............................................. C01F 1/00
[52] U.S. Cl. ..................................... 422/123; 454/337
[58] Field of Search ................. 454/337; 422/123, 124

[56] References Cited

U.S. PATENT DOCUMENTS

| | | | |
|---|---|---|---|
| 2,497,068 | 2/1950 | Canney | 454/337 |
| 3,661,323 | 5/1972 | Farris | 454/337 X |
| 3,930,797 | 1/1976 | Gertz | |
| 4,159,672 | 3/1979 | Garguilo | |
| 4,303,617 | 12/1981 | Bryson | 422/123 |
| 4,903,583 | 2/1990 | Frazier | |

FOREIGN PATENT DOCUMENTS 59-118520 of 1984 Japan .
62-50220 of 1987 Japan .
62-85709 of 1987 Japan .

Primary Examiner—John C. Fox

[57] ABSTRACT

A device (20) mounted on the exterior of, and communicating with the interior of, plenum (19) or output ducts (18), of an existing air conditioning and heating system of an enclosed structure, to combine the elements of air, and the elements of a scent producing, disinfecting, or germacidal chemical, utilizing, and upstream of, the air currents produced by the fan in the system to distribute the elements mixture at the outlets of output ducts (18) into the areas they serve. The amount of mixture flow, determined by the user, is controlled by manual manipulation of ball valve (23). The frequency of the mixture flow, determined by the user, is controlled either by the automatic cycling of the system fan, or, by manual manipulation of the fan switch on the system control.

2 Claims, 3 Drawing Sheets

ELEMENTS COMBINING DEVICE FOR ENCLOSED STRUCTURES

BACKGROUND

1. Field of Invention

This invention relates to treating the air in an enclosed structure, specifically to adding a scent, germacide, or disinfectant to the air and ducts of air conditioning and heating systems.

2. Description of Prior Art

Many ways of distributing scent into an enclosed area are known in the art.

Standard liquid, solid, or oil type air fresheners, although simple in operation, have a short effective range.

The problem was somewhat improved by the introduction of electrically heated gel fresheners, but the range is still limited.

U.S. Pat. No. 3,930,797 to Gertz, Jan. 6, 1976 is simple in operation, but, solid fresheners are short lived under the conditions illustrated in this patent.

U.S. Pat. No. 4,159,672 to Garguilo, Jul. 3, 1979, and U.S. Pat. No. 4,903,583 to Frazier, Feb. 27, 1990, appear, logically, to be effective, but are mechanically and electrically complex.

OBJECTS AND ADVANTAGES

Accordingly, several objects and advantages of my invention are:

(a) to provide a way of introducing a scent, germacidal, or disinfecting chemical into the existing ductwork of an air conditioning and heating system of a structure (b) to provide a way of introducing a scent, germacidal or disinfecting chemical into the existing ductwork of an air conditioning and heating system of a structure using the air currents provided by the fan in the system.

(c) to provide a way of metering the mixture flow of air and scent, germacidal or disinfecting chemical using an adjustable valve.

(d) to utilize many forms of scent chemicals, such as, liquids, gels, oils or solids, without modification to the device.

(e) to be inexpensive to manufacture.

(f) to be easily installed in existing air conditioning and heating systems by persons without special technical skills.

(g) to be easy to maintain.

(h) to have no moving parts.

(i) to be used in multiples, at the primary or alternate locations, if diversity is desired.

(j) to utilize naturally occuring draft currents when the air conditioning and heating system is not operating.

(k) to be activated, by the user, when the air conditioning and heating system is not operating, by manually turning the system control to the fan "ON" position for the desired time, then manually returning it to the "AUTO" position.

(l) to operate automatically whenever the system cycles the fan.

Still further objects and advantages will become apparent from consideration of the ensuing descriptions and drawings.

DRAWING FIGURES

Figure 1:
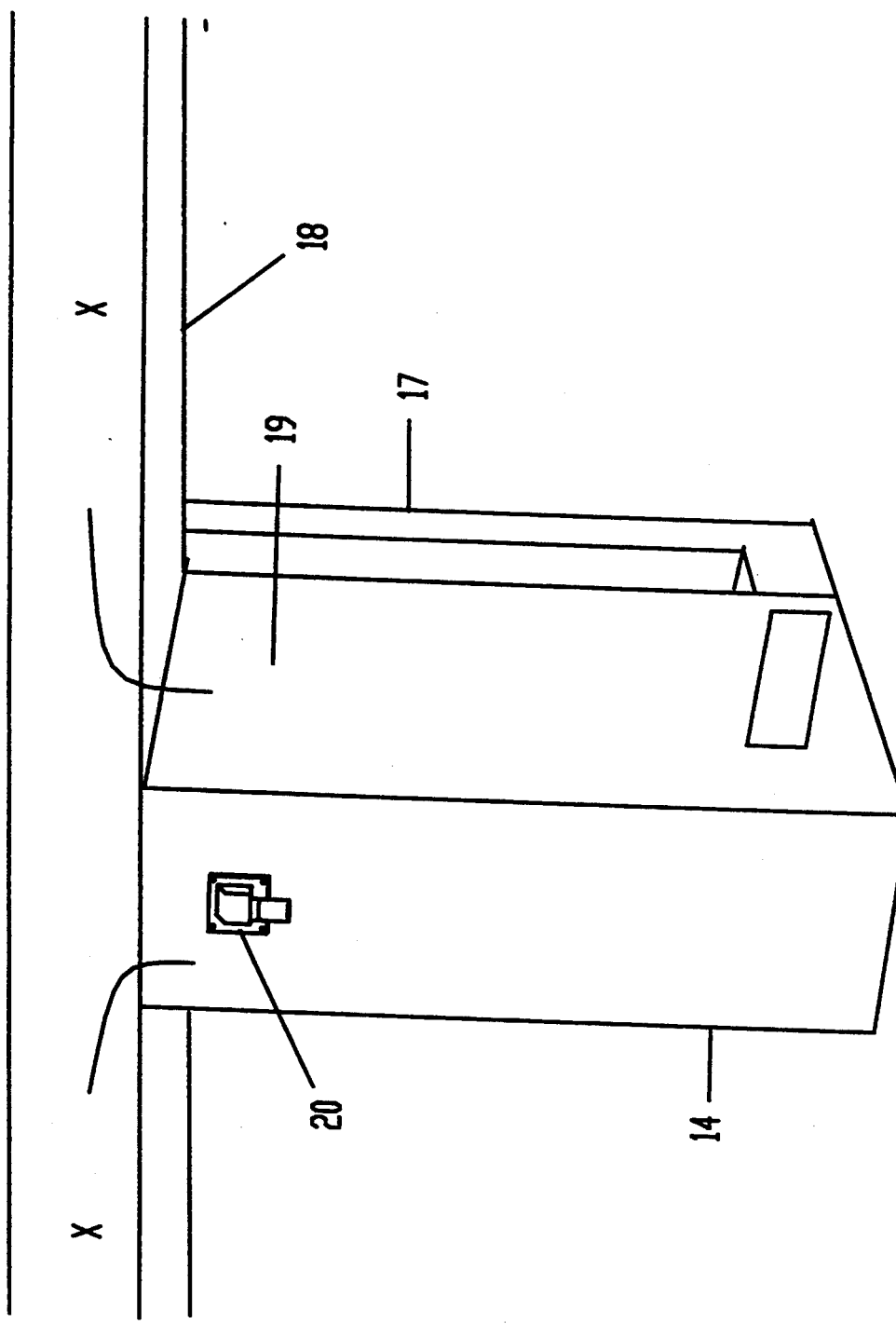
FIG. 1 shows a perspective view of the device in the primary location of a typical, updraft, air conditioning and heating system.

| Reference Numerals In Drawings | |
|---|---|
| 1 mounting plate | 24 intake tube and socket |
| 2 mounting holes | 25 discharge conduit |
| 7 intake scoop and coupler ball | 26 conduit and valve seat support |
| 8 mixing chamber | 27 conduit valve seat |
| 10 "o" ring seals | 30 adjustment shaft support |
| 11 discharge valve seat and bushing | 31 adjustment shaft |
| | 32 adjustment lever and detent pawl |
| 12 discharge tube | 33 detent disc |
| 14 air conditioning and heating unit | 34 reservoir attachment collar |
| 17 air return duct | 35 reservoir |
| 18 output ducts | 36 "T" wick |
| 19 plenum | 37 wick support |
| 20 device (entire assembly) | X alternate locations |
| 22 housing | |
| 23 ball valve | |

DESCRIPTION—FIGS. 2 TO 5

A mounting plate 1 is a square or rectangular plate, made of suitable material, to which a housing 22, and it's sub-parts are attached and has mounting holes 2 for attachment to the plenum 19 or output ducts 18 of an air conditioning and heating system with sheet metal screws.

An intake scoop and coupler ball 7 extends to the interior of, but not attached to, mounting plate 1 and to the interior of, but not attached to, housing 22 by way of a hole in mounting plate 1.

Intake scoop and coupler ball 7 may be rotated 360 degrees and is offset, vertically and horizontally, in housing 22.

An "O" ring 10 is used to seal intake scoop and coupler ball 7 to mounting plate 1 on the interior of housing 22.

A conduit and valve seat support 26 is rigidly attached to the interior, and extends to both sides and top and bottom of, housing 22.

A discharge conduit 25 is rigidly attached to conduit and valve seat support 26 and extends downward, and through the bottom of housing 22.

Conduit and valve seat support 26 has a hole that corresponds to the interior of discharge conduit 25.

A conduit valve seat 27 is round, and rigidly attached to conduit and valve seat support 26, with a hole through it's center which corresponds to the hole in conduit and valve seat support 26.

Conduit valve seat 27 is flat at the rear attachment point to conduit and valve seat support 26, and is concave at the front.

A ball valve 23 is a sphere with a hole through it's center that corresponds to the hole in conduit valve seat 27.

Ball valve 23, is free to rotate rotate in and, mates to the concave surface of conduit valve seat 27.

A discharge valve seat and bushing 11 is round and concave at the rear to mate with ball valve 23 with a hole through it's center that corresponds to the hole in ball valve 23.

Discharge valve seat and bushing 11 extends through, but not attached to, a hole, that is horizontally centered in, mounting plate 1, and is shouldered at the front for "O" ring 10.

"O" ring 10 seals discharge valve seat and bushing 11 to mounting plate 1 on the interior of housing 22.

A discharge tube 12 is attached to the front of discharge valve seat and bushing 11.

A reservoir attachment collar 34 is attached to the underside of housing 22 with corresponding holes for intake tube and socket 24, and discharge conduit 25.

Reservoir attachment collar 34 is course-threaded on the interior of it's circumference to accept an externally threaded reservoir 35 or refill.

Figure 2:
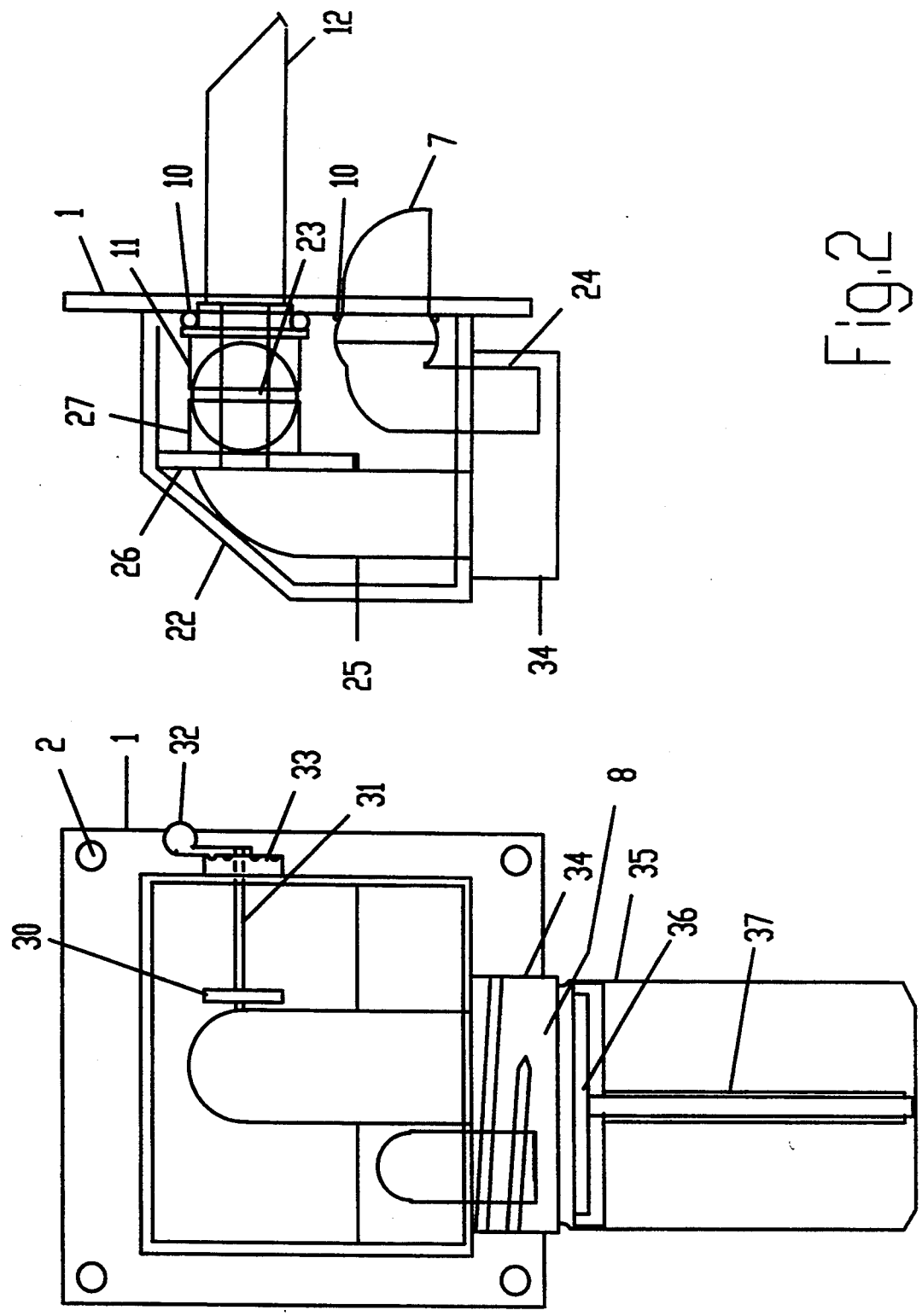
FIG. 2 shows a back and side view of the device.
Figure 5:
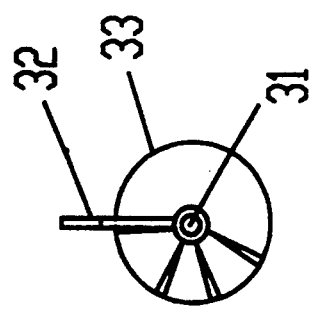
FIG. 5 shows detail of the adjustment lever and detent pawl, in the "HIGH" position, on the detent disc.
Figure 4:
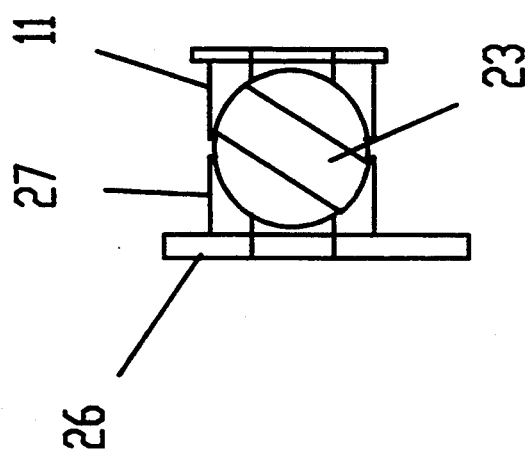
FIG. 4 shows detail of the ball valve in the "OFF" position.
Figure 3:
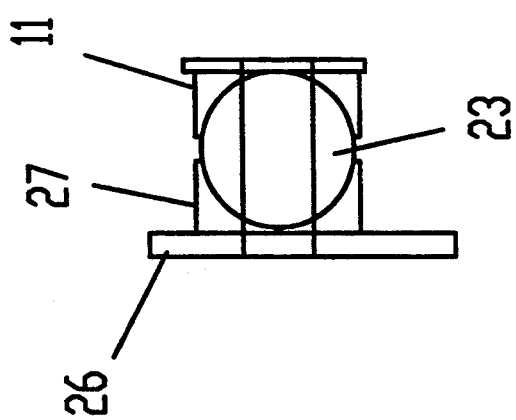
FIG. 3 shows detail of the ball valve in the "HIGH" position.

In FIG. 2, a reservoir 35, a "T" wick 36, and a wick support 37, are illustrated as a typical refill with liquid freshener, to aid in comprehension of the device, since the configuration of reservoir 35 or refill would be a matter of preferance of the manufacturer or user as to the medium to be used such as, liquid, gel, oil, or solid.

An adjustment shaft 31 is rigidly attached to the side of ball valve 23 and extends through holes in an adjustment shaft support 30, the side of housing 22, a detent disc 33 and rigidly attached to an adjustment lever and detent pawl 32 at it's pivot point.

Adjustment shaft support 30 is rigidly attached to the interior wall of housing 22 to provide inboard torsional stability to adjustment shaft 31.

A detent disc 33 is rigidly attached to the exterior side of housing 22, having a hole in it's center for adjustment shaft 31, and radial depressions, on it's outboard surface, that mate with a ridge on an adjustment lever and detent pawl 32.

Adjustment lever and detent pawl 32 has a linear ridge, on it's inboard surface, that mates to the depressions in detent disc 33, and a thumb tab opposite it's pivot point.

OPERATIONS—FIGS. 1 TO 5

The operation of my invention in the preferred embodiment is as follows.

Device 20 is attached to the exterior of plenum 19 or output duct 18, and communicates to the interior, by means of holes, in the sheet metal wall of an air conditioning and heating system, that correspond to intake scoop and coupler ball 7 and discharge tube 12.

Duiring installation of device 20, the installer would rotate intale scoop and coupler ball 7 so that the opening faces the air currents coming from the fan of the system and the opening of discharge tube 12 faces away from the fan's air currents.

When the air conditioning and heating system cycles to it's operational mode to provide heating or cooling the fan is activated.

Some of the air currents provided by the fan are collected by, and enter into, the opening of intake scoop and coupler ball 7, and intake tube and socket 24 causing the air currents to blow downward into a mixing chamber 8.

The mixing chamber 8 is simply the enclosed space within the attachment collar 34 between the bottom of housing 22 and the top of the air freshener chemical being used in reservoir 35.

Freshening scent emits from the top of the chemical being used continuously, in varied degrees, depending on formulation and temperature, into mixing chamber 8.

Air currents coming downward into mixing chamber 8 from intake tube and socket 24 cause turbulence within mixing chamber 8, combining the elements in air with the elements of the air freshening chemical.

The mixed elements then rise to the highest vertical point in, and having a lower pressure than, mixing chamber 8. That point being the opening of discharge conduit 25.

The elements mixture travels through discharge conduit 25, the hole in conduit and valve seat support 26, and the hole in conduit valve 27 where it encounters ball valve 23.

The elements mixture passes through ball valve 23 at a rate, determined by the degree of restriction caused by the adjustment position of ball valve 23, set by the user.

The volume of elements mixture flow then passes through the hole in discharge valve seat and bushing 11 and into the opening of discharge tube 12.

The elements mixture passes through discharge tube 12 and exits into plenum 19 or output ducts 18, eventually exiting the air conditioning and heating system into the enclosed structure it serves.

The user may adjust the amount of freshener flow through device 20 by manually rotating adjustment lever and detent pawl 32 to the desired position.

When weather conditions require neither cooling nor heating, or, between cycles of the air conditioning system, device 20 could be activated, by the user, by manually setting the fan switch of the control of the system to the "ON" position. After the desired level of air freshening is reached the user would set the fan switch back to the "AUTO" position.

SUMMARY, RAMIFICATIONS, AND SCOPE

Thus the reader will see that the device described above, to combine elements, is simple in design and operation, and is economical and easy to, manufacture, install, maintain, and use.

While my above description contains many specifities, these should not be construed as limitations on the scope of the invention, but rather as an exemplification of the preferred embodiment thereof. Many variations are possible.

For example:
a. A chemical medium could be used to combine with the atmosphere of the enclosed structure to produce a recognizable scent if undesirable elements,such as carbon monoxide or radon, are present.
b. By installing the device on the return air duct of the system, the chemical being used would treat the air entering the system, thus being more effective in treating bacteria that accumulate in the condensation from the air conditioning evaporator coil.
c. To eliminate, or reduce, allergens, such as,dust mites,or their enzymes, in an enclosed structure.

Thus the scope of the invention should be determined by the appended claims and their legal equivalents, rather than by the examples given.

I claim:
1. An apparatus for combining a material with an air flow in a plenum comprising
a housing including a side for attachment to a sidewall of said plenum and
a bottom,
a reservoir attached to the bottom of the housing for containing the material,
first conduit means extending into the air flow in the plenum for communicating air from the air flow in the plenum to the reservoir,
the first conduit means comprising a first conduit having an end disposed in the plenum which includes a scoop directed towards the flow of air in the plenum,
second conduit means for communicating a flow of air mixed with the material from the reservoir back to the air flow in the plenum,
the second conduit means comprising a second conduit having an angled end disposed in the plenum and directed away from the flow of air in the plenum,
the reservoir further including a space for mixing the air communicated thereto by the first conduit and the material contained therein,
means for regulating the flow of air mixed with the material in the second conduit,
the means for regulating the flow of air mixed with the material in the second conduit comprising a ball valve.

2. An apparatus as set forth in claim 1 wherein the first and second conduit means are adjustably oriented with respect to the plenum to allow for different plenum and air flow configuration.

* * * * *